(12) United States Patent
Hamann et al.

(10) Patent No.: US 9,797,812 B2
(45) Date of Patent: Oct. 24, 2017

(54) FILTER REPLACEMENT LIFETIME PREDICTION

(71) Applicant: INTERNATIONAL BUSINESS MACHINES CORPORATION, Armonk, NY (US)

(72) Inventors: Hendrik F. Hamann, Yorktown Heights, NY (US); Levente I. Klein, Tuckahoe, NY (US); Dennis G. Manzer, Bedford Hills, NY (US); Fernando J. Marianno, New York, NY (US)

(73) Assignee: International Business Machines Corporation, Armonk, NY (US)

( * ) Notice: Subject to any disclaimer, the term of this patent is extended or adjusted under 35 U.S.C. 154(b) by 330 days.

(21) Appl. No.: 13/847,255

(22) Filed: Mar. 19, 2013

(65) Prior Publication Data

US 2014/0283682 A1    Sep. 25, 2014

(51) Int. Cl.
| | |
|---|---|
| *B01D 46/00* | (2006.01) |
| *G01M 99/00* | (2011.01) |
| *B01D 46/42* | (2006.01) |
| *G01L 9/00* | (2006.01) |
| *G01N 17/04* | (2006.01) |
| *G01N 33/00* | (2006.01) |

(52) U.S. Cl.
CPC ....... *G01M 99/008* (2013.01); *B01D 46/0086* (2013.01); *B01D 46/429* (2013.01); *G01L 9/00* (2013.01); *G01N 17/04* (2013.01); *G01N 33/0004* (2013.01)

(58) Field of Classification Search
CPC .. G01N 1/2205; G01N 17/04; B01D 46/0086; B01D 46/00

USPC ..... 73/863.23–863.25; 95/1–24; 96/397–412
See application file for complete search history.

(56) References Cited

U.S. PATENT DOCUMENTS

| | | |
|---|---|---|
| 4,914,924 A | 4/1990 | Takahashi |
| 6,009,404 A | 12/1999 | Eimer |
| 6,391,102 B1 | 5/2002 | Bodden et al. |
| 6,736,980 B2 | 5/2004 | Moscaritolo |
| 7,326,269 B2 | 2/2008 | Wootton et al. |

(Continued)

OTHER PUBLICATIONS

A.R. Prest & R. Turvey, Cost-Benefit Analysis: A Survey 685-86 (The Economic Journal, 1965).*

(Continued)

*Primary Examiner* — T. Bennett McKenzie
(74) *Attorney, Agent, or Firm* — Tutunjian & Bitetto, P.C.; Vazken Alexanian (57) ABSTRACT

Methods and systems for predicting a filter lifetime include building a filter effectiveness history based on contaminant sensor information associated with a filter; determining a rate of filter consumption with a processor based on the filter effectiveness history; and determining a remaining filter lifetime based on the determined rate of filter consumption. Methods and systems for increasing filter economy include measuring contaminants in an internal and an external environment; determining a cost of a corrosion rate increase if unfiltered external air intake is increased for cooling; determining a cost of increased air pressure to filter external air; and if the cost of filtering external air exceeds the cost of the corrosion rate increase, increasing an intake of unfiltered external air.

11 Claims, 6 Drawing Sheets

(56) References Cited

U.S. PATENT DOCUMENTS

| | | | |
|---|---|---|---|
| 7,686,872 B2 | 3/2010 | Kang | |
| 7,979,250 B2 | 7/2011 | Archibald et al. | |
| 2007/0044656 A1* | 3/2007 | Farmer | F02C 7/05 |
| | | | 95/1 |
| 2007/0101688 A1* | 5/2007 | Wootton et al. | 55/385.2 |
| 2008/0041138 A1* | 2/2008 | Marra | 73/31.02 |
| 2008/0078289 A1* | 4/2008 | Sergi et al. | 95/25 |
| 2010/0316534 A1* | 12/2010 | Niazi | 422/122 |
| 2011/0308308 A1* | 12/2011 | Herman | F02M 35/0208 |
| | | | 73/114.31 |
| 2012/0038377 A1* | 2/2012 | Hamann | G01N 27/00 |
| | | | 324/700 |
| 2012/0111190 A1* | 5/2012 | Dariavach | B01D 46/429 |
| | | | 95/10 |
| 2012/0318135 A1* | 12/2012 | Hoglund | F24F 3/1603 |
| | | | 95/19 |
| 2013/0103352 A1* | 4/2013 | ter Horst | G01N 15/0826 |
| | | | 702/182 |

OTHER PUBLICATIONS

Greg Welch & Gary Bishop, An Introduction to the Kalman Filter, Dept. of Computer Science, University of North Carolina at Chapel Hill (Jul. 24, 2006), https://www.cs.unc.edu/~welch/media/pdf/kalman_intro.pdf.*

Eland, R., et al. "Air Filters Effects on Data Center Supply Fan Power" 2012 13th IEEE Intersociety Conference on Thermal and Thermomechanical Phenomena in Electronic Systems. May-Jun. 2012. pp. 377-384.

Hamann, H., et al. "Recovery Act: A Measurement—Management Technology for Improving Energy Efficiency in Data Centers and Telecommunication Facilities" Final technical Report—Award No. DE-EE0002897. Jun. 2012. pp. 1-27.

* cited by examiner

FILTER REPLACEMENT LIFETIME PREDICTION

STATEMENT OF GOVERNMENT RIGHTS

This invention was made with Government support under Contract No.: DEEE0002897 awarded by Department of Energy. The Government has certain rights in this invention.

BACKGROUND

Technical Field

The present invention relates to the use of outdoor air for cooling data centers and, more particularly, to maintaining contamination level in the facility by using air contamination data and to predicting the effective lifetime of air conditioner filters in data centers.

Description of the Related Art

With the increasing computational power of IT equipment, the energy consumed for cooling can grow to be similar to the energy consumed for computation. One way to reduce cooling is the use of outdoor air for cooling when temperature, relative humidity, and air contamination are within acceptable ranges. One concern for using outside air for cooling is the introduction of gaseous and particulate contamination in the data centers. In general air filters can be used for removing the contamination for the air but they can impede air flow across the filter, requiring larger blower to maintain air flow, and can increase the overall maintenance cost of the data centers.

Air filters can effectively remove particular and gaseous contamination, but they are expensive to maintain. Contamination may be highly location-dependent, with different contaminants present in different quantities depending on the geographic area. As a result, filter replacement time can vary substantially according to data center settings and the orientation of its air intake. A recommended filter replacement time is usually provided by manufacturers based on an average value between best- and worst-case scenarios and may not actually reflect the realities of a given installation.

The American Society of Heating, Refrigerating and Air-Conditioning Engineers (ASHRAE) issues guidelines regarding gaseous and particular contamination in data centers. In 2011, the ASHRAE indicated that data centers should maintain an environment having a copper reactivity rate of less than 300 angstroms per month and a silver reactivity rate of less than 200 angstroms per month to maintain reliable equipment operation. Corrosion can be caused by both gaseous and particular contamination, and particulate contamination may have further negative mechanical and electrical effects.

Cooling systems that perform heat transfer with external air provide economical heat dissipation but involve a greater exposure to external contaminants. Leaks are inevitable and impose a slow air exchange between the clean air inside the data center and the contaminated external air.

SUMMARY

A filter monitoring system includes a filter effectiveness history based on contaminant sensor information associated with a filter received from one or more contaminant sensors; and a lifetime module comprising a processor configured to determine a rate of filter consumption based on the filter effectiveness history and to determine a remaining filter lifetime based on the determined rate of filter consumption.

A method for increasing filter economy includes measuring contaminants in an internal and an external environment; determining a cost of a corrosion rate increase if unfiltered external air intake is increased for cooling; determining a cost of increased air pressure to filter external air; and if the cost of filtering external air exceeds the cost of the corrosion rate increase, increasing an intake of unfiltered external air.

A system for increasing filter economy includes a memory configured to receive measurements of contaminants in an internal and an external environment; a cost effectiveness module comprising a processor configured to determine a cost of a corrosion rate increase if unfiltered external air intake is increased for cooling, to determine a cost of increased air pressure to filter external air, and to determine if the cost of filtering external air exceeds the cost of the corrosion rate increase; and an air intake module configured to increase an intake of unfiltered external air if it is determined that the cost of filtering external air exceeds the cost of the corrosion rate increase.

These and other features and advantages will become apparent from the following detailed description of illustrative embodiments thereof, which is to be read in connection with the accompanying drawings.

BRIEF DESCRIPTION OF DRAWINGS

The disclosure will provide details in the following description of preferred embodiments with reference to the following figures wherein.

DETAILED DESCRIPTION OF PREFERRED EMBODIMENTS

Embodiments of the present invention provide dynamic cooling in data centers situated in locations where the outside air has high gaseous and particulate contamination during some periods of times of the year and where outside air is used for cooling. Embodiments of the present invention provide effectiveness monitoring for air filters that tracks manufacturer specifications, real-time sensor data, and predictive estimates of filter lifetime. Based on real-time measurements and predictions, the useful lifetime of a filter can be effectively doubled, thus reducing the cost of maintenance. Cost-effective corrosion and particulate sensors may be employed for both particulate and gaseous contaminants to build an accurate determination of current filter effectiveness. Such effectiveness may be tracked over time to build an estimate of the filter's useful lifetime. This allows site-specific monitoring and management of filters.

Figure 1:
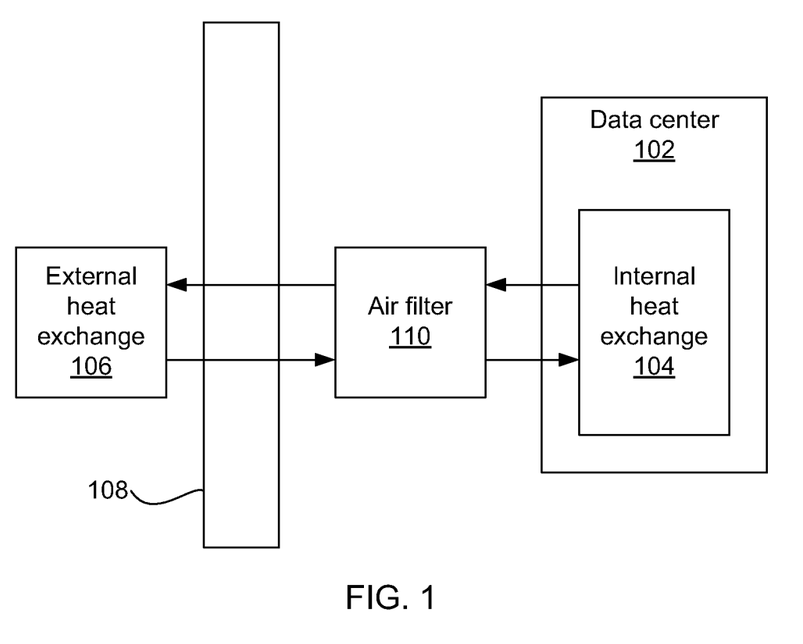
FIG. 1 is a diagram of a cooling system for a data center that uses external air cooling in accordance with the present principles.

Referring now to the drawings in which like numerals represent the same or similar elements and initially to FIG. 1, an exemplary cooling system is shown. A data center 102 uses an internal heat exchange 104 to transfer heat from one or more data center systems to air. The internal heat exchange 104 may include one or more of, e.g., radiators, liquid-cooling systems, fans, etc. The internal heat exchange may transfer heat to the ambient air in the data center 102 or may use a closed system to isolate transferred heat.

Data center 102 is isolated from the external environment by a barrier 108. The barrier 108 should be understood as being an imperfect barrier that allows a slow, but non-negligible, amount of air transfer between the data center 102 and the external environment. This leakage provides a route for air-based contaminants to enter the otherwise closed environment of the data center 102. The leakage may come from intentional openings in the barrier 108 (e.g., using outside air for cooling) or may be unintentional (e.g., leaks in the wall or imperfect isolation of the data center).

The internal heat exchange 104 provides heated air to an external heat exchange 106. External heat exchange 106 allow outside air to be introduced directly in the data center to cool the IT equipment. The air may pass through one or more air filters 110 that are designed to remove gaseous and/or particular contaminants. Such filters 110 may be based on any appropriate filtering mechanism, including for example chemical filters, mechanical filters, catalytic filters, etc. For the purpose of illustration, the filters 110 are shown as being directly in the path of the internal/external heat exchange, but such filters 110 may also be placed to process standing air in the data center 102.

The data center 102 includes a number of systems, any of which may be susceptible to contaminants. Corrosion increasingly takes place due to the increase of the air contamination across the globe, utilization of outside air for cooling, and use of non-lead solders in circuit boards. For example, copper creep corrosion is a corrosion of copper plating to copper sulfide on printed circuit boards, causing copper sulfite to creep over the surface of the circuit boards, potentially creating electric shorts between adjacent circuit-board features. As another example, the corrosion of silver terminations to silver sulfide in surface-mounted components leads to the loss of silver metallization and, ultimately, the breaking of an electrical connection in components such as resistors.

Corrosion may be caused by such gaseous contaminants as nitric oxide, nitrogen dioxide, and sulfur dioxide. Most of the above gases are commonly encountered in the atmosphere due to industrial activities, car emission, agricultural activities, etc. Corrosion rate is furthermore driven by temperature and humidity, where higher temperature and higher relative humidity increases the corrosion rate. Particular contaminants, such as ionic dust, may cause further corrosion, particularly when the relative humidity is high enough for the dust to become wet and, therefore, electrically conductive.

Figure 2:
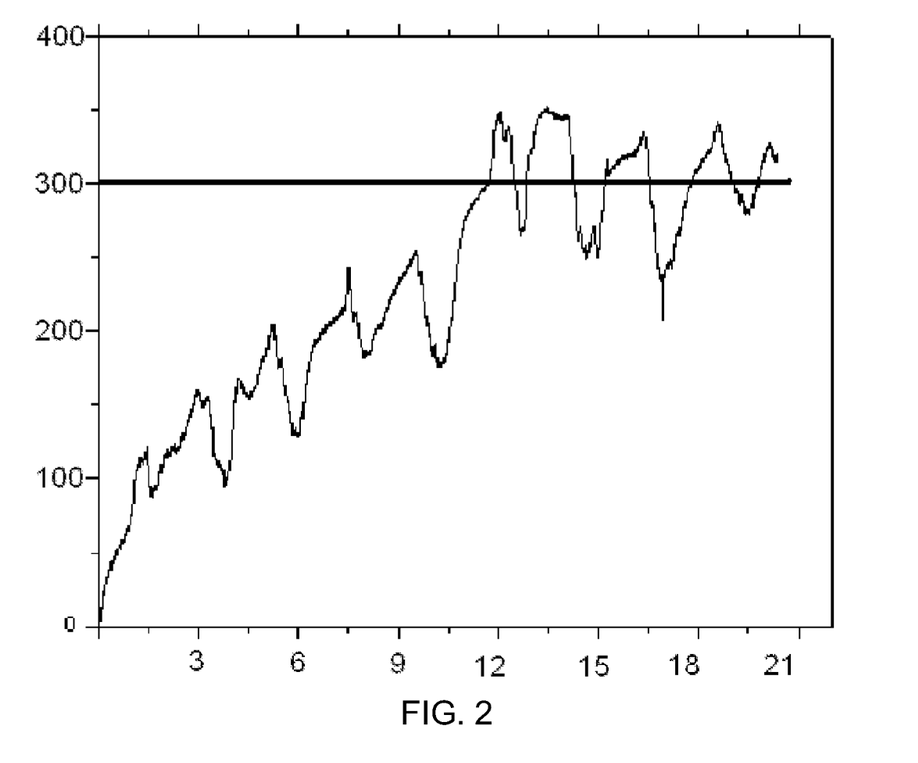
FIG. 2 is a graph of filter effectiveness over time.

Referring now to FIG. 2, a graph illustrating filter aging is shown. This graph represents a copper corrosion rate on the vertical axis in angstroms per month and a filter lifetime on the horizontal axis measured in months. The filter 110 in this example has a recommended lifetime of six months. When the filter 110 is brand new it will most effectively capture the contaminants in the air and, such that the corrosion rate will be very low. As the filter 110 ages, the filter 110 will retain less of the corrosive molecules in the air and the corrosion rate will increase. An increased corrosion rate may also be the result of an increase in the levels of outside pollution. However, in this particular environment, the filter 110 is still maintaining a corrosion rate below the recommended level of 300 angstroms per month after six months. Indeed, the filter 110 appears to function within the guidelines after a full year of operation, indicating that it has a useful lifetime effectively double the recommended lifetime. If this information is available to data center managers, it not only provides them with the ability to determine when filters 110 actually need to be replaced, but allows them to predict a future time when such replacement will be most economical.

Figure 3:
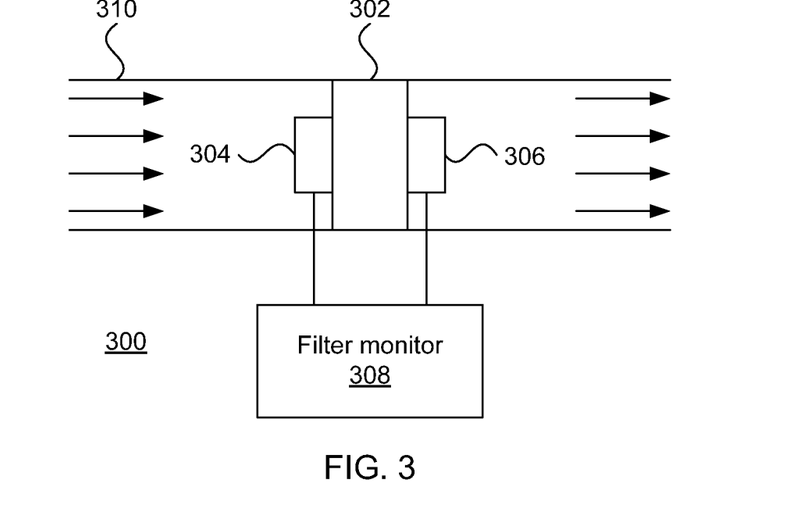
FIG. 3 is a diagram of a sensor-equipped filter with monitoring apparatus in accordance with the present principles.

Referring now to FIG. 3, a filter lifetime prediction system 300 is shown. A filter 302 is placed in an air duct 310. An intake sensor 304 is placed at the intake side of the filter 302 and an outlet sensor 306 is placed on the outlet side. The sensors 304 and 306 monitor the pressure drop across the filter 302, making sure that enough air is passed through the filter to ensure cooling of the data center. If the pressure drop increases, it is an early indicator that the filter is clogged and that the effectiveness of the air filtration provided by filter 302 may decrease. This information provides warning as to when the filter 302 should be replaced.

It should be recognized that different type of sensors 304/306 may be employed. These sensors may include, but are not limited to, corrosion sensors for gaseous contamination monitoring and dust/particle sensors for particulate contamination. A differential pressure sensor may measure the pressure drop across the filter 302 and indicate whether the filter 302 is clogged or for some other reason not passing a useful amount of air. The sensors 304/306 will have effective lifetimes of their own, as corrosion sensors may be consumed through use. The sensors 304/306 may be selected to be directly correlated with the expected effective lifetime of the filter. The sensors 304/306 may be assembled in a relatively compact form. For example, the whole sensor assembly may be of the order of a half-inch to a side and may be fastened directly to the air filter 302. As such, the filter 302 and the sensors 304/306 may be provided as a single package and replaced as a single unit.

Sensors 304/306 communicate with a filter monitor 308 that tracks and stores sensor data. The filter monitor 308 analyzes that data and provides outputs regarding the current status and expected lifetime of the filter 302. The sensors 304/306 may communicate with the filter monitor 308 via wired or wireless connections. It should be recognized that wireless connections are often preferable, as wiring may be difficult to install in locations that filters are often used (such as duct 310), but wireless communications may similarly be difficult in such contexts. Wireless communication protocols should be conducive to low-power communications, as a true wireless solution will need self-contained power in the form of, e.g., an on-sensor battery. The sensors may communicate using any appropriate protocol, including without limitation Bluetooth, Wi-Fi®, ZigBee®, etc.

Figure 4:
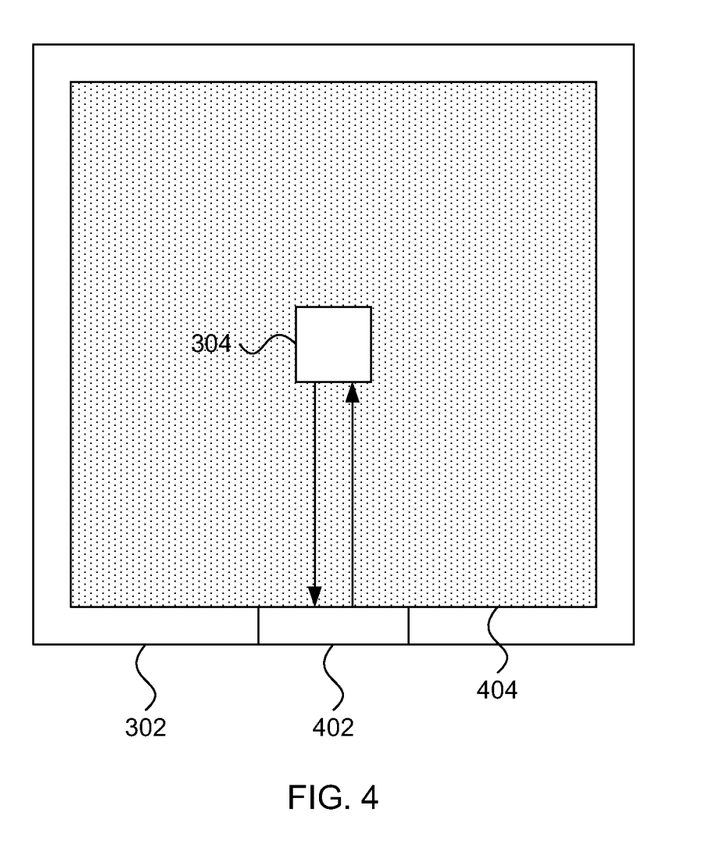
FIG. 4 is a diagram of a sensor-equipped filter in accordance with the present principles.

Referring now to FIG. 4, an exemplary air filter 302 is shown. The filter 302 is illustrated face-on, with a filtering material 404 shown. The intake sensor 304 is mounted directly on the filtering material 404 in this example, though it should be recognized that the sensor may also be mounted on the frame of the filter 302. A control module 402 is mounted on the frame of the filter 302 and communicates with the sensor 304. The control module 402 may provide electrical power to the sensor 304. Furthermore, if the filter 302 is slotted into position when installed, the control module 402 may be mounted in such a manner as to remain exposed. This allows the control module 402 to provide effective wireless data communication from a duct that would otherwise shield such signals.

For any sensor 306 that measures the effectiveness of a filter 302, the signal will increase as the filter stays in the field. A threshold value can be present, as shown above in FIG. 2. The signal may be compared to a threshold value, either in filter monitor 308 or in control module 402. If the sensor signal is below the threshold value, then the filter status is determined to be functional. If the signal exceeds the threshold, then the filter is determined to be in need of replacement. Exceeding the threshold may also indicate that outside air may not be used for cooling. The filter monitor 308 issues a warning that the filter 302 is not performing within an acceptable range may issue an instruction to shut off cooling using outside air.

It should be recognized that the control module 402 may be the same component as the filter monitor 308, such that the control module 402 represents a self-contained unit. Alternatively, several control modules 402 may communicate with the filter monitor 308 in a distributed fashion.

Figure 5:
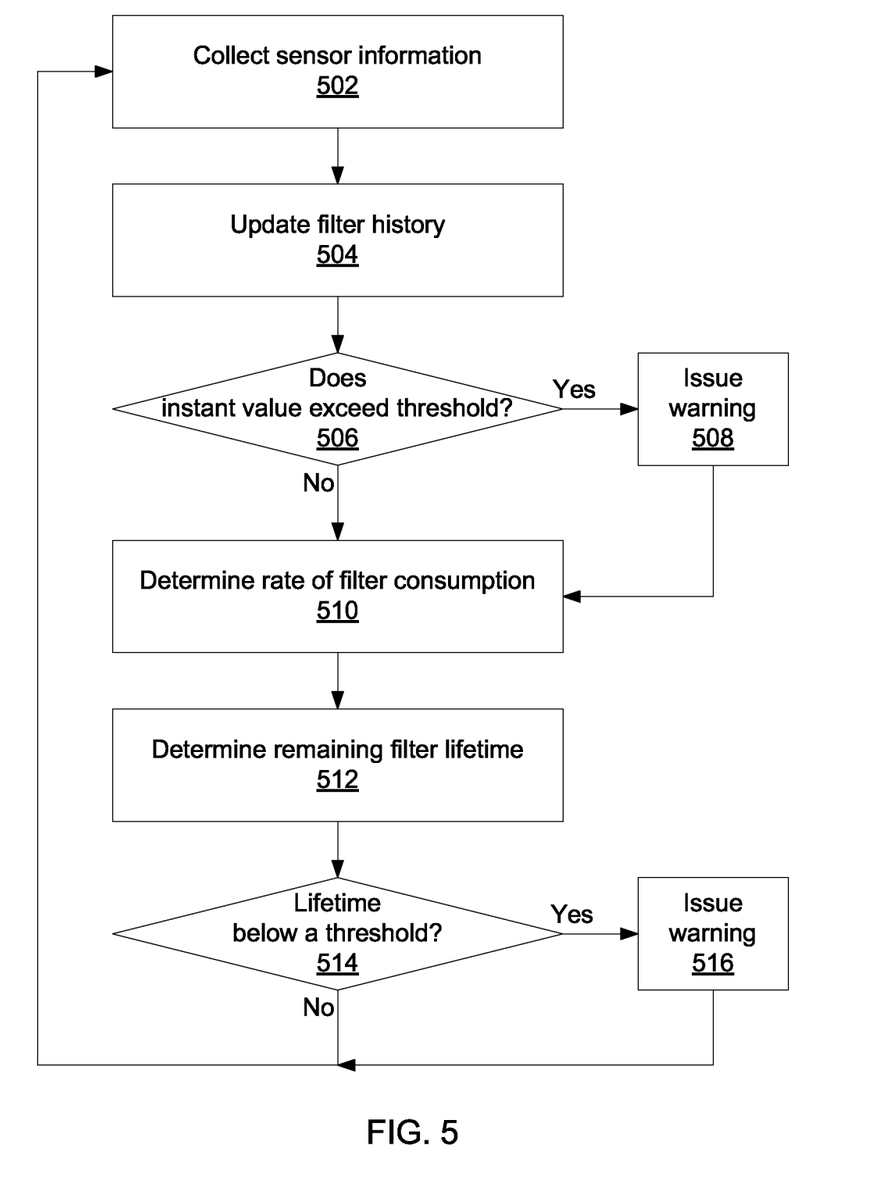
FIG. 5 is a block/flow diagram of determining a filter lifetime in accordance with the present principles.

Referring now to FIG. 5, a method for estimating a future filter lifetime is shown. Block 502 collects information from sensors 304/306. This information reflects the nature of the particular sensor and may represent, for example, air pressure differential, the presence of specific contaminants, corrosion rates, particulate density, etc. Sensor information 502 may be collected periodically, for example on a daily or seasonal basis. Block 504 updates historical information for one or more filters 302 associated with the sensors 304/306. This historical information may simply be a list of periodically measured sensor values or it can show gaseous pollutant variation over a certain period of time. The prediction of filter lifetime is based on real time corrosion rate calculations from the corrosion sensor using Kalman filters to predict short term variation of the corrosion rate. The extrapolation is used to estimate when the filter performance will fall below acceptable levels.

Block 506 checks whether the instantaneous values of the sensors 304/306 exceed (or fall below) a threshold. The internal corrosion rate may be determined based on the outdoor corrosion rate. One formula for finding the outdoor corrosion rate is as follows:

$$CR_{out} \approx (H_2S)^a (SO_2)^b (NO_2)^c e^{d \cdot RH} e^{E_a/k_B T},$$

where $H_2S$, $SO_2$, and $NO_2$ is are the gaseous contaminants hydrogen sulfide, sulfur dioxide, and nitrous oxide in parts per billion, RH is the relative humidity, $E_a$ is the activation energy for a given metal, $k_B$ is the Boltzmann constant, and the scaling variables a, b, c, and d are determined by fitting historical corrosion data versus variation of the gaseous pollutant concentration in a controlled or normal environment. The base corrosion rate can be determined when the gaseous contaminant concentration is at acceptable levels for a data center.

The internal corrosion rate may be determined as follows:

$$CR_{in} = \frac{CR_{out}}{1 + T^f RH^g (H_2S)^h (SO_2)^i (NO_2)^j},$$

where the scaling variables f, g, h, i, and j are determined by measuring the corrosion rate indoors and correlating it with the outdoor corrosion rate and gaseous concentration. These indoor scaling variables may be different from those outside, as chemical contaminants may also arise from internal sources, such as cleaning chemicals.

If the corrosion rate exceeds (or falls below) the threshold, block 508 issues a warning. If the instantaneous value of the sensors 304/306 goes past this threshold, it may indicate pollution levels are high. In this case, the outside air used for cooling should be shut off. If the corrosion rate remains high it may be an indication that the filter 302 has become damaged. In one example, physical damage to the filter 302 might result in an air pressure differential that is too low, while a physical obstruction of the filter 302 might result in a differential that is too high. Either condition should be addressed quickly, and the warning issued by block 508 may provide an operator with information regarding the fault and how to fix it. In a similar way, particularly harsh environmental conditions (such as a forest fire or pollen season) may be accounted for, allowing for automated shutoff of outside air intake to limit further contamination.

Block 510 uses the filter history to determine a rate of filter consumption. Block 510 may employ a statistical analysis to compare the filter history to known filter characteristics or may use a time series analysis such as a Kalman filter model. Using a Kalman filter model, future values may be predicted and a remaining lifetime may be computed in block 512. The Kalman filter allows the elimination of noise associated with, e.g., corrosion rate measurements that may arise due to changes in temperature and relative humidity that accelerate or reduce corrosion rate on a short-term basis. In addition, a Kalman filter model may estimate the effectiveness of the filter 302 under reduced air flow conditions, such as when the amount of air flow is reduced due to clogging by particulate matter.

Block 514 determines the remaining filter lifetime falls below a filter lifetime threshold. If not, processing returns to block 502 to continue collecting sensor information. If so, block 516 issues a warning.

As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing. Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks. The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

The flowchart and block diagrams in the Figures illustrate the architecture, functionality, and operation of possible implementations of systems, methods and computer program products according to various embodiments of the present invention. In this regard, each block in the flowchart or block diagrams may represent a module, segment, or portion of code, which comprises one or more executable instructions for implementing the specified logical function(s). It should also be noted that, in some alternative implementations, the functions noted in the blocks may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

Figure 6:
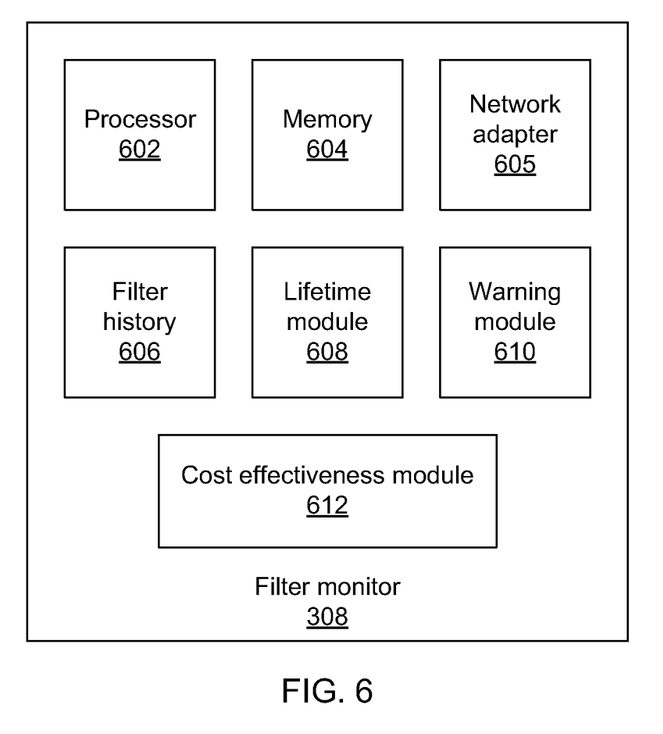
FIG. 6 is a diagram of a filter monitor in accordance with the present principles.

Referring now to FIG. 6, a block diagram of a filter monitor 308 is shown. The filter monitor includes a hardware processor 602 and memory 604. A network adapter 605 communicates with one or more sensors 304/306 and receives sensor measurement information. A filter history 606 is maintained in memory 604 based on the information received from sensors 304/306, maintaining a table of sensor values for one or more associated filters 302. Lifetime module 608 uses processor 602 to calculate an estimated lifetime for the filter 302 based on analysis of the filter history 606. A warning module 610 may be configured to respond to instantaneous sensor information that exceeds or falls below acceptable thresholds. If this occurs, warning module 610 notifies a user or system operator of the problem, allowing quick resolution. A cost effectiveness module 612 allows the filter monitor 308 to alter air intake patterns, for example by bypassing the filter 302 if external conditions permit.

Figure 7:
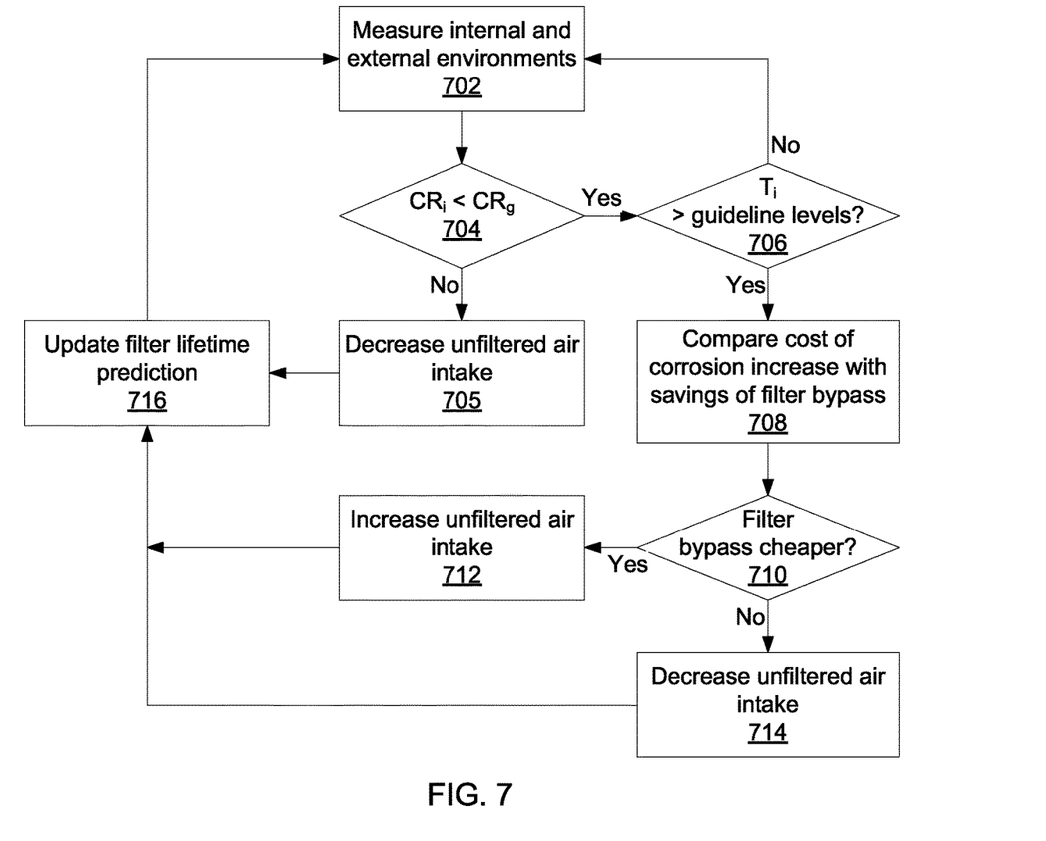
FIG. 7 is a block/flow diagram of a method for improving cooling economy in accordance with the present principles.

Referring now to FIG. 7, a block/flow diagram of a method for filter bypass is shown. In some cases, the contaminants in the external environment may be low enough that such air may be used directly, without filtration. Thus, if the costs incurred by using unfiltered air are lower than the cost of the energy expended forcing air through a filter, it becomes more economical to simply use the unfiltered air.

Block 702 measures the internal and external environments using sensors 304/306. These measurements may include, for example, corrosion rates, temperature, and relative humidity. Block 704 compares, e.g., the internal corrosion rate to a guideline corrosion rate. If the internal corrosion rate is higher than the guideline level, block 705 decreases the intake of unfiltered air from the external environment. This represents a scenario where, for example, the level of contaminants in the outside air increases, such that more filtration is needed. This is a separate consideration from that described above with respect to FIG. 5—a transient spike in external corrosion rate may temporarily raise the internal corrosion rate beyond guideline levels without necessitating filter replacement.

If the internal corrosion rate at block 704 is below the guideline limit, then block 706 determines whether additional cooling is needed. If the internal temperature is not above guideline levels, the no change is needed and processing returns to block 702 to measure the environments again after some delay. It should be recognized that this consideration need not be limited to temperature. For example, the same consideration may be applied for internal relative humidity.

If the temperature has risen above guideline levels, then block 708 performs a cost/benefit analysis regarding the use of unfiltered air. Using unfiltered air takes less energy, as the air does not need to be forced through a filter. As a result, the economic efficiency of using unfiltered air may be compared to a cost of increased internal corrosion. If block 710 determines that the cost of filtering the air is greater than the cost of the marginal increase in internal corrosion rate, block 712 increases the intake of unfiltered air. Otherwise, block 714 decreases the intake of unfiltered air.

Changing the unfiltered air intake in block 705, 712, or 714 will have an impact on the predicted lifetime of the filter 302. Block 716 updates the filter lifetime prediction described above with respect to block 512. As the intake of unfiltered air increases, the estimated lifetime of the filter 302 can be expected to increase, as less air will be pushed through. On the other hand, as the intake of unfiltered air decreases, the difference will be made up in an increase of air through the filter 302, thereby decreasing the expected lifetime.

Having described preferred embodiments of a system and method for filter replacement lifetime prediction (which are intended to be illustrative and not limiting), it is noted that modifications and variations can be made by persons skilled in the art in light of the above teachings. It is therefore to be understood that changes may be made in the particular embodiments disclosed which are within the scope of the invention as outlined by the appended claims. Having thus described aspects of the invention, with the details and particularity required by the patent laws, what is claimed and desired protected by Letters Patent is set forth in the appended claims.

What is claimed is:

1. A method for controlling air filtration in an enclosure having a filtered air intake and an unfiltered air intake, comprising:
   measuring contaminants in an internal and an external environment using respective internal and external contaminant sensors;
   determining an increase in a corrosion rate for one or more objects in the enclosure if unfiltered external air intake is increased for cooling based on the measured contaminants in the internal and external environments, comprising calculating a corrosion rate of the external environment as:

$$CR_{out} \approx (H_2S)^a (SO_2)^b (NO_2)^c e^{d \cdot RH} e^{E_a/k_B T}$$

where $H_2S$, $SO_2$, and $NO_2$ are the gaseous contaminants hydrogen sulfide, sulfur dioxide, and nitrous oxide in parts per billion, RH is the relative humidity, $E_a$ is the activation energy for a given metal, $k_B$ is the Boltzmann constant, T is temperature, and the scaling variables a, b, c, and d are determined by fitting historical corrosion data versus variation of the gaseous pollutant concentration in a controlled or normal environment;
   determining an air pressure needed to filter external air using a filter in the filtered air intake;
   controlling an intake of unfiltered external air by bypassing the filter in the filtered air intake, based on the corrosion rate increase and the air pressure needed to filter external air;
   updating a predicted filter lifetime based on the intake of unfiltered external air, comprising:
      building a filter effectiveness history based on contaminant sensor information associated with a filter;
      determining a rate of filter consumption with a processor based on the filter effectiveness history; and
      determining a remaining filter lifetime based on the determined rate of filter consumption; and
   providing a warning if the contaminant sensor information associated with the filter exceeds an instantaneous failure threshold or if the determined remaining filter lifetime falls below a filter lifetime threshold.

2. The method of claim 1, wherein the rate of filter consumption characterizes a change over time in a degree of unfiltered contamination.

3. The method of claim 1, wherein the remaining filter lifetime is a time remaining until the degree of unfiltered contamination is predicted to exceed a threshold.

4. The method of claim 1, wherein the instantaneous failure threshold represents a physical failure of the filter.

5. The method of claim 1, wherein the contaminant sensor information includes sensor information for gaseous and particulate contaminants.

6. The method of claim 5, further comprising determining whether external conditions are within guideline levels for temperature, relative humidity, and corrosion rate.

7. The method of claim 1, further comprising decreasing the intake of unfiltered external air if external conditions fall outside of guideline levels.

8. A computer readable storage medium comprising a computer readable program, wherein the computer readable program when executed on a computer causes the computer to perform the steps of claim 1.

9. The method of claim 1, wherein measuring contaminants comprises measuring a contaminant concentration.

10. The method of claim 1, wherein determining the rate of filter consumption comprises performing a time series analysis on the filter effectiveness history.

11. The method of claim 10, wherein performing a time series analysis comprises applying a Kalman filter model to predict future filter consumption values.

* * * * *